US010136877B2

(12) United States Patent
Tanaka et al.

(10) Patent No.: US 10,136,877 B2
(45) Date of Patent: Nov. 27, 2018

(54) ULTRASOUND DIAGNOSIS APPARATUS AND IMAGE PROCESSING APPARATUS

(71) Applicant: Toshiba Medical Systems Corporation, Otawara-shi (JP)

(72) Inventors: Go Tanaka, Otawara (JP); Kazuya Akaki, Utsunomiya (JP); Yoshihiro Oomori, Otawara (JP); Satoshi Matsunaga, Nasushiobara (JP); Tetsuya Higashi, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 1061 days.

(21) Appl. No.: 14/446,677

(22) Filed: Jul. 30, 2014

(65) Prior Publication Data

US 2014/0343428 A1   Nov. 20, 2014

Related U.S. Application Data

(63) Continuation of application No. PCT/JP2013/052411, filed on Feb. 1, 2013.

(30) Foreign Application Priority Data

Feb. 1, 2012   (JP) .................................. 2012-019537
Feb. 1, 2013   (JP) .................................. 2013-018729

(51) Int. Cl.
*A61B 8/00*  (2006.01)
*A61B 8/08*  (2006.01)
(Continued)

(52) U.S. Cl.
CPC ................ *A61B 8/523* (2013.01); *A61B 8/14* (2013.01); *A61B 8/463* (2013.01); *A61B 8/483* (2013.01);
(Continued)

(58) Field of Classification Search
None
See application file for complete search history.

(56) References Cited

U.S. PATENT DOCUMENTS

2007/0265530 A1\* 11/2007 Hashimoto .............. A61B 8/14
                                                                600/443
2010/0185094 A1\*  7/2010 Hamada ................... A61B 8/14
                                                                600/443

FOREIGN PATENT DOCUMENTS

JP      10-085210 A      4/1998
JP      2010-167032 A    8/2010

OTHER PUBLICATIONS

International Search Report dated Apr. 16, 2013 for PCT/JP2013/052411filed on Feb. 1, 2013 with English Translation.

(Continued)

*Primary Examiner* — Jonathan Cwern
(74) *Attorney, Agent, or Firm* — Oblon, McClelland, Maier & Neustadt, L.L.P.

(57) ABSTRACT

An ultrasound diagnosis apparatus according to an embodiment includes a parameter setting unit, a Fly Thru image generating unit, and a controlling unit. The parameter setting unit sets a value of an image quality adjusting parameter used for generating a PVR image obtained by projecting the inside of a lumen from a predetermined viewpoint, on the basis of information about the lumen rendered in an MPR image generated by using volume data. The Fly Thru image generating unit generates the PVR image by using the value of the image quality adjusting parameter that was set. The controlling unit then causes a monitor to display the PVR image.

10 Claims, 10 Drawing Sheets

(51) Int. Cl.
G06T 19/00 (2011.01)
G01S 7/52 (2006.01)
A61B 8/14 (2006.01)
G01S 15/89 (2006.01)

(52) U.S. Cl.
CPC ............ *A61B 8/488* (2013.01); *A61B 8/5238* (2013.01); *G01S 7/52074* (2013.01); *G01S 15/8993* (2013.01); *G06T 19/003* (2013.01); G01S 7/52073 (2013.01); G01S 15/8925 (2013.01); G01S 15/8979 (2013.01); G06T 2210/41 (2013.01)

(56) References Cited

OTHER PUBLICATIONS

International Written Opinion dated Apr. 16, 2013 for PCT/JP2013/052411 filed on Feb. 1, 2013.

\* cited by examiner

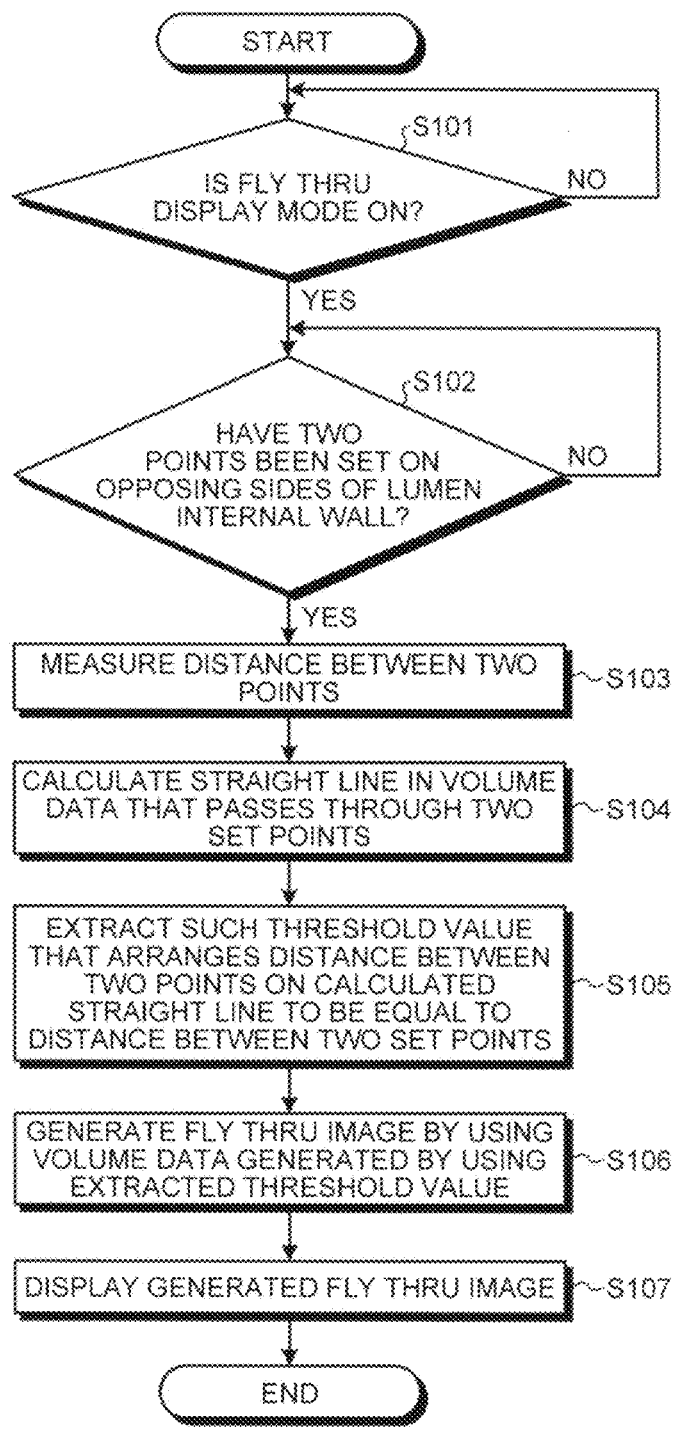

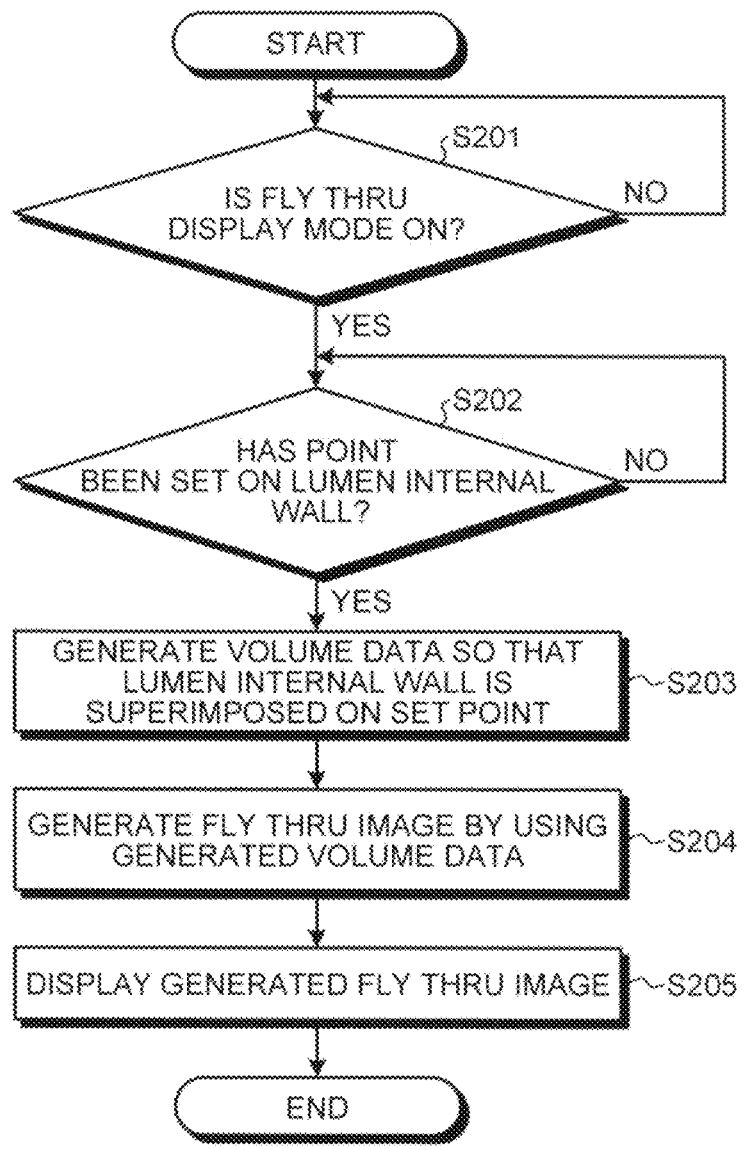

ULTRASOUND DIAGNOSIS APPARATUS AND IMAGE PROCESSING APPARATUS

CROSS-REFERENCE TO RELATED APPLICATIONS

This application is a continuation of PCT international application Ser. No. PCT/JP2013/052411 filed on Feb. 1, 2013 which designates the United States, incorporated herein by reference, and which claims the benefit of priority from Japanese Patent Application No. 2012-019537, filed on Feb. 1, 2012 and Japanese Patent Application No. 2013-018729, filed on Feb. 1, 2013, the entire contents of which are incorporated herein by reference.

FIELD

Embodiments described herein relate generally to an ultrasound diagnosis apparatus and an image processing apparatus.

BACKGROUND

Conventionally, ultrasound diagnosis apparatuses acquire three-dimensional data (volume data) by using a two-dimensional (2D) array probe or a mechanical four-dimensional (4D) probe so that users are able to view the inside of a lumen such as the portal vein in the liver or a lactiferous duct by using the acquired volume data. To realize such a viewing of the inside of a lumen, examples of methods being used include a virtual endoscopic display method by which the inside of the lumen is displayed as if the lumen was viewed through an endoscope. In the following explanation, a virtual endoscopic display may be referred to as a Fly Thru display.

To realize the Fly Thru display, a viewpoint and a line-of-sight direction are set on the inside of the lumen contained in volume data, so as to generate and display a perspective projection image (a Perspective Volume Rendering (PVR) image). During a Fly Thru display process, a Fly Thru image is displayed which is a moving image obtained by updating the generated PVR image while moving the viewpoint position along the lumen.

Also, the Fly Thru display makes it possible to view, together with the Fly Thru image, the internal wall of the entire lumen, by generating and displaying Multi-Planar Reconstruction (MPR) images on three cross-sectional planes orthogonal to the line-of-sight direction. However, according to the conventional technique described above, there are some situations where the lumen in a Fly Thru image is not properly displayed.

BRIEF DESCRIPTION OF THE DRAWINGS

FIG. 7 is a flowchart of a procedure in a process performed by the ultrasound diagnosis apparatus according to the first embodiment;

FIG. 9 is a flowchart of a procedure in a process performed by an ultrasound diagnosis apparatus according to the second embodiment;

DETAILED DESCRIPTION

According to embodiment, An ultrasound diagnosis apparatus comprising, a setting unit, a virtual endoscopic image generating unit and a display controlling unit. The setting unit configured to, on a basis of information about a lumen rendered in a two-dimensional tomographic image generated by using three-dimensional image data, set a value of an image quality adjusting parameter used for generating a virtual endoscopic image obtained by projecting an inside of the lumen from a predetermined viewpoint. The virtual endoscopic image generating unit configured to generate the virtual endoscopic image by using the value of the image quality adjusting parameter that was set. The display controlling unit configured to cause a predetermined display unit to display the virtual endoscopic image.

Figure 1:
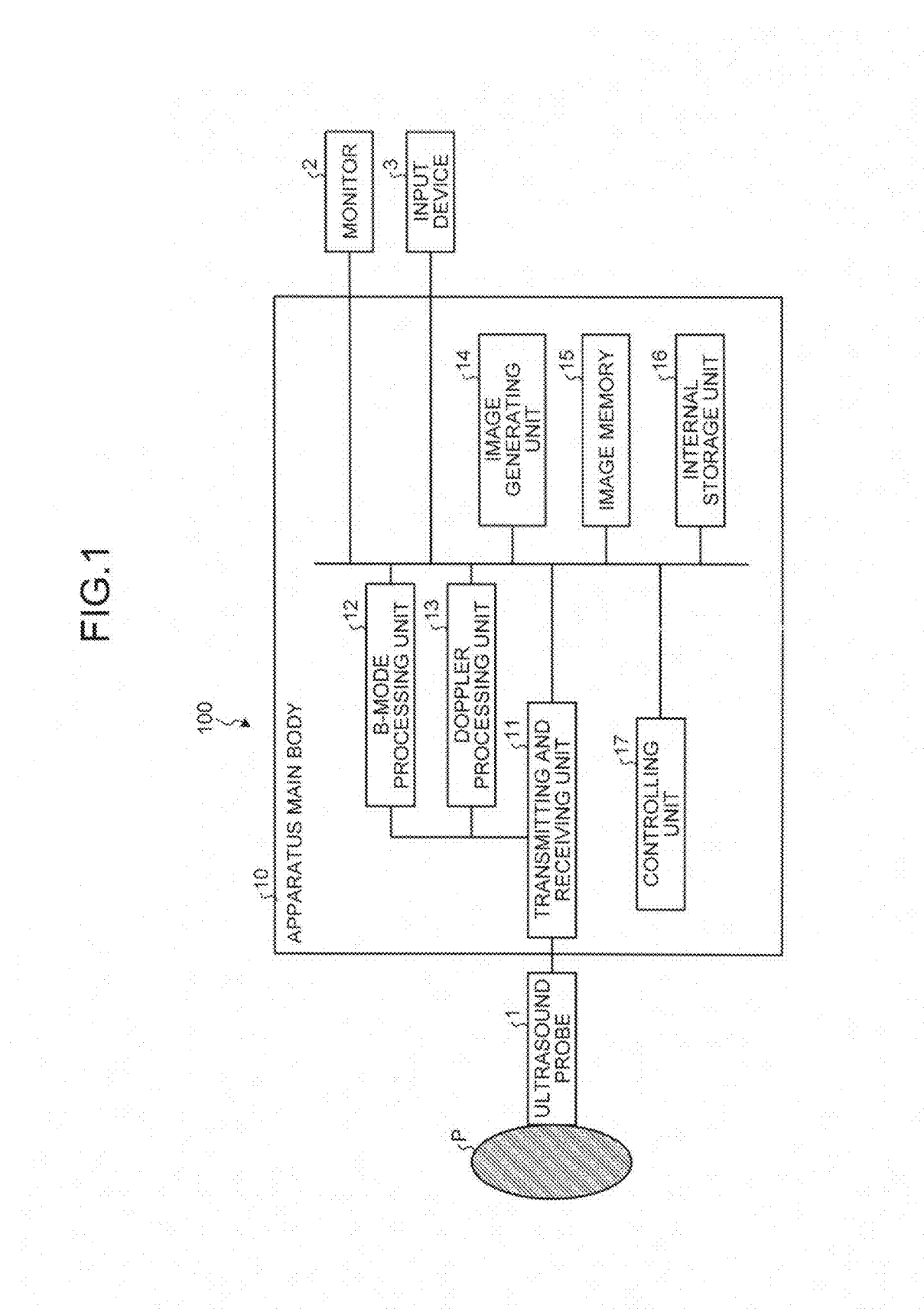
FIG. 1 is a drawing for explaining an overall configuration of an ultrasound diagnosis apparatus according to a first embodiment.

First, a configuration of an ultrasound diagnosis apparatus according to a first embodiment will be explained. FIG. 1 is a drawing for explaining a configuration of an ultrasound diagnosis apparatus 100 according to the first embodiment. As shown in FIG. 1, the ultrasound diagnosis apparatus 100 according to the first embodiment includes an ultrasound probe 1, a monitor 2, an input device 3, and an apparatus main body 10.

The ultrasound probe 1 includes a plurality of piezoelectric transducer elements, which generate an ultrasound wave based on a drive signal supplied from a transmitting and receiving unit 11 included in the apparatus main body 10 (explained later). Further, the ultrasound probe 1 receives a reflected wave from a subject P and converts the received reflected wave into an electric signal. Further, the ultrasound probe 1 includes a matching layer with which the piezoelectric transducer elements are provided and a backing material that prevents backward propagation of ultrasounds from the piezoelectric transducer elements. The ultrasound probe 1 is detachably connected to the apparatus main body 10.

When an ultrasound wave is transmitted from the ultrasound probe 1 to the subject P, the transmitted ultrasound wave is sequentially reflected on a surface of discontinuity of acoustic impedances at a tissue in the body of the subject P and is received as a reflected-wave signal by the plurality of piezoelectric transducer elements included in the ultrasound probe 1. The amplitude of the received reflected-wave signal is dependent on the difference between the acoustic impedances on the surface of discontinuity on which the ultrasound wave is reflected. When the transmitted ultrasound pulse is reflected on the surface of a flowing bloodstream or a cardiac wall, the reflected-wave signal is, due to the Doppler effect, subject to a frequency shift, depending on a velocity component of the moving object with respect to the ultrasound wave transmission direction.

In this situation, the ultrasound probe 1 according to the first embodiment is an ultrasound probe configured to be able to scan the subject P two-dimensionally and to scan the subject P three-dimensionally, while using the ultrasound waves. More specifically, the ultrasound probe 1 according to the first embodiment is a mechanical scan probe that scans the subject P three-dimensionally by causing a plurality of piezoelectric transducer elements each of which scans the subject P two-dimensionally to swing at a predetermined angle (a swinging angle). Alternatively, the ultrasound probe 1 according to the first embodiment may be a two-dimensional ultrasound probe configured to be able to perform an ultrasound scan on the subject P three-dimensionally by using a plurality of piezoelectric transducer elements that are arranged in a matrix formation. It should be noted that the two-dimensional ultrasound probe is able to scan the subject P two-dimensionally by transmitting the ultrasound waves in a focused manner.

The monitor 2 displays a Graphical User Interface (GUI) used by an operator of the ultrasound diagnosis apparatus 100 to input various types of setting requests through the input device 3 and displays an ultrasound image and the like generated by the apparatus main body 10. For example, the monitor 2 displays a Fly Thru image or MPR images generated as a result of a process performed by an image generating unit 14 (explained later).

The input device 3 includes a trackball, a switch, a dial, and a touch command screen, and the like. The input device 3 receives the various types of setting requests from the operator of the ultrasound diagnosis apparatus and transfers the received various types of setting requests to the apparatus main body 10. For example, the input device 3 receives an input operation for specifying a predetermined position in a two-dimensional image. In an example, the input device 3 receives an input operation for specifying a position on a lumen internal wall of a lumen rendered in an MPR image.

The apparatus main body 10 is an apparatus that generates the ultrasound image based on the reflected wave received by the ultrasound probe 1. More specifically, the apparatus main body 10 according to the first embodiment is an apparatus configured to be able to generate a three-dimensional ultrasound image (volume data), based on the three-dimensional reflected-wave data received by the ultrasound probe 1. As shown in FIG. 1, the apparatus main body 10 includes the transmitting and receiving unit 11, a B-mode processing unit 12, a Doppler processing unit 13, the image generating unit 14, an image memory 15, an internal storage unit 16, and a controlling unit 17.

The transmitting and receiving unit 11 includes a trigger generating circuit, a delaying circuit, a pulser circuit, and the like and supplies the drive signal to the ultrasound probe 1. The pulser circuit repeatedly generates a rate pulse for forming a transmission ultrasound wave at a predetermined rate frequency. Further, the delaying circuit applies a delay period that is required to focus the ultrasound wave generated by the ultrasound probe 1 into the form of a beam and to determine transmission directionality and that corresponds to each of the piezoelectric transducer elements, to each of the rate pulses generated by the pulser circuit. Further, the trigger generating circuit applies a drive signal (a drive pulse) to the ultrasound probe 1 with timing based on the rate pulses. In other words, the delaying circuit arbitrarily adjusts the directions of the transmissions from the piezoelectric transducer element surfaces, by varying the delay periods applied to the rate pulses.

The transmitting and receiving unit 11 has a function to be able to instantly change the transmission frequency, the transmission drive voltage, and the like, for the purpose of executing a predetermined scanning sequence based on an instruction from the controlling unit 17 (explained later). In particular, the configuration to change the transmission drive voltage is realized by using a linear-amplifier-type transmitting circuit of which the value can be instantly switched or by using a mechanism configured to electrically switch between a plurality of power source units.

The transmitting and receiving unit 11 includes an amplifier circuit, an Analog/Digital (A/D) converter, an adder, and the like and generates reflected-wave data by performing various types of processes on the reflected-wave signal received by the ultrasound probe 1. The amplifier circuit amplifies the reflected-wave signal for each of channels and performs a gain correcting process thereon. The A/D converter applies an A/D conversion to the gain-corrected reflected-wave signal and applies a delay period required to determine reception directionality to digital data. The adder performs an adding process on the reflected-wave signals processed by the A/D converter so as to generate the reflected-wave data. As a result of the adding process performed by the adder, reflected components from the direction corresponding to the reception directionality of the reflected-wave signals are emphasized.

In this manner, the transmitting and receiving unit 11 controls the transmission directionality and the reception directionality in the transmission and the reception of the ultrasound wave. In the present example, the transmitting and receiving unit 11 according to the first embodiment causes the ultrasound probe 1 to transmit three-dimensional ultrasound beams to the subject P and generates the three-dimensional reflected-wave data from the three-dimensional reflected-wave signals received by the ultrasound probe 1.

The B-mode processing unit 12 receives the reflected-wave data from the transmitting and receiving unit 11 and generates data (B-mode data) in which the strength of each signal is expressed by a degree of brightness, by performing a logarithmic amplification, an envelope detection process, and the like on the received reflected-wave data. In the present example, the B-mode processing unit 12 is able to change the frequency bandwidth to be visualized, by changing the frequency for the wave detection. Further, the B-mode processing unit 12 is able to perform, in parallel, wave detecting processes at two different wave-detection frequencies on one piece of reflected-wave data.

The Doppler processing unit 13 extracts bloodstreams, tissues, and contrast echo components under the influence of the Doppler effect by performing a frequency analysis so as to obtain velocity information from the reflected-wave data received from the transmitting and receiving unit 11, and further generates data (Doppler data) obtained by extracting moving object information such as an average velocity, the turbulence, the power, and the like for a plurality of points.

The B-mode processing unit 12 and the Doppler processing unit 13 according to the first embodiment are able to process both two-dimensional reflected-wave data and three-dimensional reflected-wave data. In other words, the B-mode processing unit 12 according to the first embodiment is able to generate three-dimensional B-mode data from the three-dimensional reflected-wave data. The Doppler processing unit 13 according to the first embodiment is able to generate three-dimensional Doppler data from the three-dimensional reflected-wave data.

The image generating unit 14 generates ultrasound images from the data generated by the B-mode processing unit 12 and the Doppler processing unit 13. In other words, from the B-mode data generated by the B-mode processing unit 12, the image generating unit 14 generates a B-mode image in which the strength of the reflected-wave is expressed by a degree of brightness. More specifically, from the three-dimensional B-mode data generated by the B-mode processing unit 12, the image generating unit 14 generates a three-dimensional B-mode image.

Further, from the Doppler data generated by the Doppler processing unit 13, the image generating unit 14 generates an average velocity image, a turbulence image, and a power image, expressing the moving object information, or a color Doppler image, which is an image combining these images. More specifically, from the three-dimensional Doppler data generated by the Doppler processing unit 13, the image generating unit 14 generates a three-dimensional color Doppler image. In the following sections, the three-dimensional B-mode image and the three-dimensional color Doppler image generated by the image generating unit 14 will be collectively referred to as "volume data".

Further, the image generating unit 14 is able to generate various types of images used for displaying the generated volume data on the monitor 2. More specifically, the image generating unit 14 is able to generate MPR images or a rendering image from the volume data.

In other words, as a result of the ultrasound probe 1 performing the three-dimensional ultrasound scan on an image taking site of the subject P, the transmitting and receiving unit 11 generates the three-dimensional data. Further, as the image used for displaying the volume data on the monitor 2, the image generating unit 14 generates, for example, MPR images on three orthogonal cross-sectional planes, a rendering image obtained by using the contact surface of the ultrasound probe 1 on the subject P as a viewpoint, or a rendering image obtained by using an arbitrary location as a viewpoint, per instructions from the operator.

Further, the image generating unit 14 generates, for example, a Fly Thru image, which is a projection image obtained by arranging a viewpoint on the inside of a lumen with respect to the lumen contained in volume data. The Fly Thru image generating process performed by the image generating unit 14 will be explained in detail later. In addition, the image generating unit 14 is also able to generate a synthesized image obtained by synthesizing text information of various parameters, scale graduations, body marks, and the like with an ultrasound image. The Fly Thru image generated by the image generating unit 14 may be referred to as a virtual endoscopic image or a PVR image.

The image memory 15 is a memory for storing therein the ultrasound image generated by the image generating unit 14. Further, the image memory 15 is also able to store therein the data generated by the B-mode processing unit 12 and the Doppler processing unit 13.

The internal storage unit 16 stores therein various types of data such as a control computer program (hereinafter, "control program") to realize ultrasound transmissions and receptions, image processing, and display processing, as well as diagnosis information (e.g., subjects' IDs, medical doctors' observations), diagnosis protocols, and various types of body marks. Further, the internal storage unit 16 may be used, as necessary, for storing therein any of the images stored in the image memory 15.

The controlling unit 17 is a controlling processor (a Central Processing Unit (CPU)) that realizes functions of an information processing apparatus (a computer) and is configured to control the entire processes performed by the ultrasound diagnosis apparatus. More specifically, based on the various types of setting requests input by the operator via the input device 3 and various types of control programs and various types of data read from the internal storage unit 16, the controlling unit 17 controls processes performed by the transmitting and receiving unit 11, the B-mode processing unit 12, the Doppler processing unit 13, and the image generating unit 14. Further, the controlling unit 17 exercises control so that the monitor 2 displays the ultrasound images stored in the image memory 15 and the various types of image data stored in the internal storage unit 16, or a GUI used for realizing the processes performed by the image generating unit 14 and the processing results of the image generating unit 14, and the like.

An overall configuration of the ultrasound diagnosis apparatus 100 according to the first embodiment has thus been explained. The ultrasound diagnosis apparatus 100 according to the first embodiment configured as described above is arranged to be able to properly display a lumen in a Fly Thru image as a result of processes performed by the image generating unit 14 explained in detail below.

First, situations with a conventional technique where a lumen in a Fly Thru image is not properly displayed will be explained. Conventionally, when displaying a Fly Thru image, an ultrasound diagnosis apparatus performs a process to extract a lumen from obtained volume data. When performing the lumen extracting process, the ultrasound diagnosis apparatus determines whether each voxel belongs to the internal wall of the lumen (hereinafter, "lumen internal wall") or to the inside of the lumen, depending on the brightness level assigned to the voxel. In other words, the ultrasound diagnosis apparatus determines voxels each having a brightness level lower than a predetermined level as belonging to the inside of the lumen and determines voxels being in contact with the inside of the lumen and each having a brightness level equal to or higher than the predetermined level as belonging to the lumen.

Figure 2:
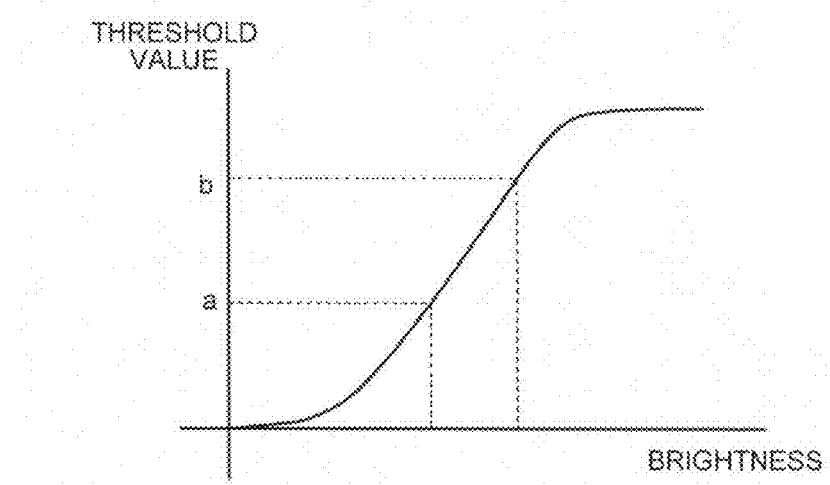
FIG. 2 is a drawing for explaining an image quality adjusting parameter.

In this situation, the ultrasound diagnosis apparatus is configured to adjust the brightness level used for determining the lumen internal wall while using an image quality adjusting parameter, because the distribution of brightness levels is different for each of obtained pieces of volume data. FIG. 2 is a drawing for explaining the image quality adjusting parameter. FIG. 2 illustrates a relationship between threshold values serving as an image quality adjusting parameter and brightness levels used for determining the lumen internal wall. In FIG. 2, the vertical axis expresses the threshold values, whereas the horizontal axis expresses the brightness levels.

As shown in FIG. 2, the brightness levels are kept in correspondence with the threshold values. For example, as shown in FIG. 2, when the threshold value is changed from "a" to "b", the value of the brightness level used for determining the lumen internal wall becomes larger. A threshold value is determined for each of the pieces of volume data, on the basis of the distribution of brightness levels contained in the volume data. In other words, the ultrasound diagnosis apparatus is configured so that a threshold value is determined in accordance with the brightness levels of obtained volume data and so that a region having the brightness levels corresponding to the determined threshold value is determined as the lumen internal wall.

With the conventional ultrasound diagnosis apparatus, however, the threshold value is fixed at the value determined according to the brightness levels of the volume data, as described above. Thus, depending on the brightness levels contained in each volume data, there are some situations where most of the voxels are determined as belonging to a lumen internal wall, and the inside of the lumen is not displayed. In those situations, the lumen cannot be properly displayed in the Fly Thru image.

Further, with the conventional ultrasound diagnosis apparatus, because the lumen internal wall is determined according to the threshold value, if the threshold value changes, the boundary between the inside of the lumen and the lumen internal wall also changes, and thus the diameter of the lumen fluctuates. As a result, with the conventional ultrasound diagnosis apparatus, there are some situations where the diameter of a lumen rendered in an MPR image is not equal to the diameter of the lumen rendered in a Fly Thru image (a PVR image). In those situations, the lumen cannot be properly displayed in the Fly Thru image.

Figure 3:
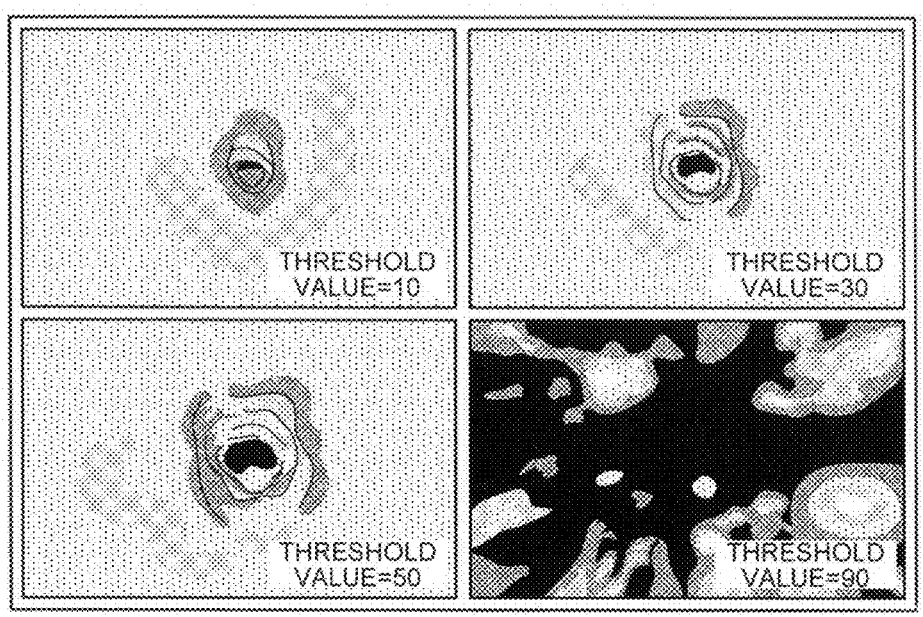
FIG. 3 is a drawing of examples of problems in a conventional technique.

FIG. 3 is a drawing of examples of the problems in the conventional technique. FIG. 3 illustrates situations where a lumen contained in mutually the same piece of volume data is displayed while the threshold value is changed. For example, as shown in FIG. 3, with a conventional ultrasound diagnosis apparatus, an apparent diameter of the lumen seen in the display image becomes larger, as the threshold value is increased from "10" to "30", "50", and "90". As explained above, with the conventional ultrasound diagnosis apparatus, there are some situations where a lumen in a Fly Thru image has a diameter different from the actual diameter of the lumen and cannot be properly displayed. Thus, the viewer is required to adjust the apparent diameter of the lumen or the like on the display screen, by operating an adjusting dial or the like.

To cope with these situations, the ultrasound diagnosis apparatus 100 according to the first embodiment makes it possible to properly display a lumen in a Fly Thru image as a result of the processes performed by the image generating unit 14 explained in detail below. In the first embodiment, an example in which a threshold value is used as the image quality adjusting parameter will be explained.

Figure 4:
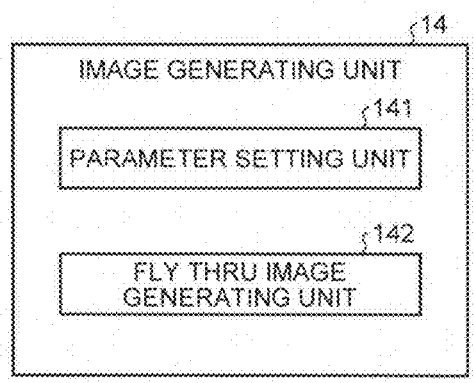
FIG. 4 is a drawing of an exemplary configuration of an image generating unit according to the first embodiment.

FIG. 4 is a drawing of an exemplary configuration of the image generating unit 14 according to the first embodiment. As shown in FIG. 4, the image generating unit 14 includes a parameter setting unit 141 and a Fly Thru image generating unit 142.

The parameter setting unit 141 extracts a two-dimensional cross-sectional image rendering a lumen by using three-dimensional image data. Further, on the basis of information of the two-dimensional image, the parameter setting unit 141 sets a value of an image quality adjusting parameter used for generating a virtual endoscopic image (a PVR image) obtained by projecting the inside of the lumen from a predetermined line-of-sight direction. More specifically, the parameter setting unit 141 sets the image quality adjusting parameter in such a manner that the distance between two points each of which is set on a different one of the opposing sides of the internal wall of the lumen rendered in the two-dimensional image is equal to the distance between the two points in the volume data.

In this situation, to cause the parameter setting unit 141 to perform the process, the viewer at first specifies a piece of volume data to serve as a processing target via the input device 3 and further requests that MPR images on three orthogonal cross-sectional planes (plane A, plane B, and plane C) should be displayed. Having received the display request via the input device 3, the controlling unit 17 controls the image generating unit 14 so that the MPR images on the three orthogonal cross-sectional planes are generated from the piece of volume data specified by the viewer. After that, the monitor 2 displays the MPR images on the three orthogonal cross-sectional planes generated by the image generating unit 14, under the control of the controlling unit 17.

By using a rendering function of the input device 3, the viewer sets the points used by the parameter setting unit 141 for setting the image quality adjusting parameter, on each of the opposing sides of the internal wall of the lumen rendered in one or more of the MPR images displayed on the monitor 2. The controlling unit 17 obtains position information of the two points in the volume data, the two points having been received by the input device 3. The controlling unit 17 then notifies the parameter setting unit 141 of the obtained position information of the two points and the distance between the two points.

Figure 5A:
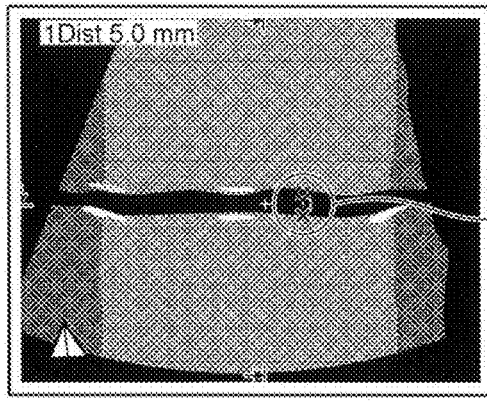
FIG. 5A is a drawing of an exemplary setting process performed on a lumen internal wall according to the first embodiment.

FIG. 5A is a drawing of an exemplary setting process performed on a lumen internal wall according to the first embodiment. FIG. 5A illustrates one of the MPR images on the three orthogonal cross-sectional planes displayed on the monitor 2. For example, the viewer selects the one of the MPR images on the three orthogonal cross-sectional planes. After that, as shown in a circle 20 in FIG. 5A, the viewer sets a point (marked with an X in the drawing) on each of the opposing sides of the internal wall of the lumen rendered in the selected MPR image.

Further, the viewer causes the ultrasound diagnosis apparatus 100 to measure the distance between the two set points. In other words, as shown in FIG. 5A for example, the controlling unit 17 measures the distance between the two set points as "Dist (distance): 5.0 mm". After that, the controlling unit 17 notifies the parameter setting unit 141 of the position information (the three-dimensional coordinates) of the two set points and the measured result "5.0 mm".

By using the position information of the two points and the distance "5.0 mm" between the two points that were notified by the controlling unit 17, the parameter setting unit 141 sets a threshold value. More specifically, the parameter setting unit 141 calculates a straight line in the volume data that passes through the notified two points and sets the threshold value in such a manner that the distance between the two points on the calculated straight line is equal to the notified distance in the MPR image.

Figure 5B:
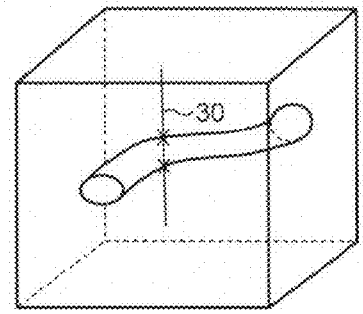
FIG. 5B is a drawing for explaining an example of a process performed by a parameter setting unit according to the first embodiment.

FIG. 5B is a drawing for explaining an example of the process performed by the parameter setting unit 141 according to the first embodiment. FIG. 5B illustrates a process performed using the two points set in FIG. 5A and the calculated distance "5.0 mm". For example, as shown in FIG. 5B, the parameter setting unit 141 calculates a straight line 30 in the volume data that passes through the notified two points. After that, the parameter setting unit 141 causes pieces of volume data to be generated by changing the threshold value at stages, extracts such a threshold value that arranges the distance between the two points on the calculated straight line 30 to be equal to "5.0 mm" as shown in FIG. 5B, and sets the extracted threshold value as a threshold value used for generating a Fly Thru image.

Figure 5C:
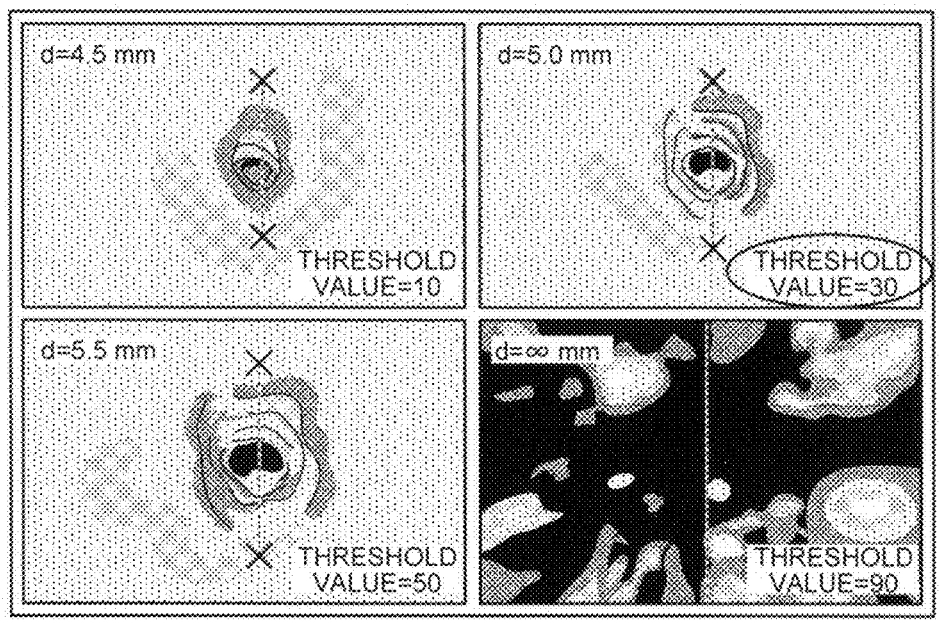
FIG. 5C is a schematic drawing of an example of a process performed by the parameter setting unit according to the first embodiment.

FIG. 5C is a schematic drawing of an example of the process performed by the parameter setting unit 141 according to the first embodiment. FIG. 5C illustrates a Fly Thru image (PVR images) each section of which is generated from a different one of pieces of volume data that are generated by changing the threshold value at stages. As shown in FIG. 5C, the parameter setting unit 141 generates the pieces of volume data by changing the threshold value at stages, such as "10", "30", "50", and "90". After that, the parameter setting unit 141 extracts such a threshold value that arranges the distance between the two points to be equal to "5.0 mm" in the generated pieces of volume data. In other words, as shown in FIG. 5C, the parameter setting unit 141 extracts the "threshold value=30" and sets the extracted "30" to be the threshold value used for generating the Fly Thru image.

By setting the threshold value as described above, the parameter setting unit 141 determines the position of the lumen internal wall in the volume data. The parameter setting unit 141 thereby extracts a lumen region contained in the volume data. Further, in the volume data from which the lumen region is extracted, a core line is set, so that PVR images are generated along the core line and so that a Fly Thru image, which is a moving image, is displayed.

Returning to the description of FIG. 4, the Fly Thru image generating unit 142 generates the PVR images by using the value of the image quality adjusting parameter that was set. More specifically, by moving the viewpoint at constant distance intervals and at constant time intervals in an arbitrary direction, along the trajectory of the core line set in the lumen region that was extracted while using the image quality adjusting parameter set by the parameter setting unit 141, the Fly Thru image generating unit 142 generates the PVR images obtained by projecting the inside of the lumen from each of the line-of-sight directions by using the volume data.

In this situation, to cause the Fly Thru image generating unit 142 to perform the process, the viewer sets the viewpoint and the line-of-sight direction. After that, the Fly Thru image generating unit 142 generates a PVR image obtained by projecting the inside of the lumen in the line-of-sight direction set from the viewpoint on the set core line. At that time, the Fly Thru image generating unit 142 performs a perspective projection radially from the viewpoint, toward the range with a near plane and a far plane defined by a Field Of View (FOV) angle, which is centered on the line-of-sight direction. After that, the Fly Thru image generating unit 142 generates the PVR images by projecting the inside of the lumen from each of the line-of-sight directions while moving the viewpoint at the constant distance intervals and at the constant time intervals. The Fly Thru image generating unit 142 then stores the generated PVR images into the image memory 15.

After that, the controlling unit 17 causes the monitor 2 to display the PVR images generated by the Fly Thru image generating unit 142 by projecting the inside of the lumen from each of the line-of-sight directions and the MPR images on the three orthogonal cross-sectional planes in the viewpoint positions at which the PVR images were generated. In this situation, by updating the PVR images at the time intervals used by the Fly Thru image generating unit 142 for moving the viewpoint to generate the PVR images, the controlling unit 17 is able to have a moving image (a Fly Thru image) displayed in which the viewer is able to view the inside of the lumen while the viewpoint is being moved along the line-of-sight direction. While the Fly Thru image is being displayed, the MPR images on the three orthogonal cross-sectional planes are also updated in conjunction with the movement of the viewpoint.

Figure 6:
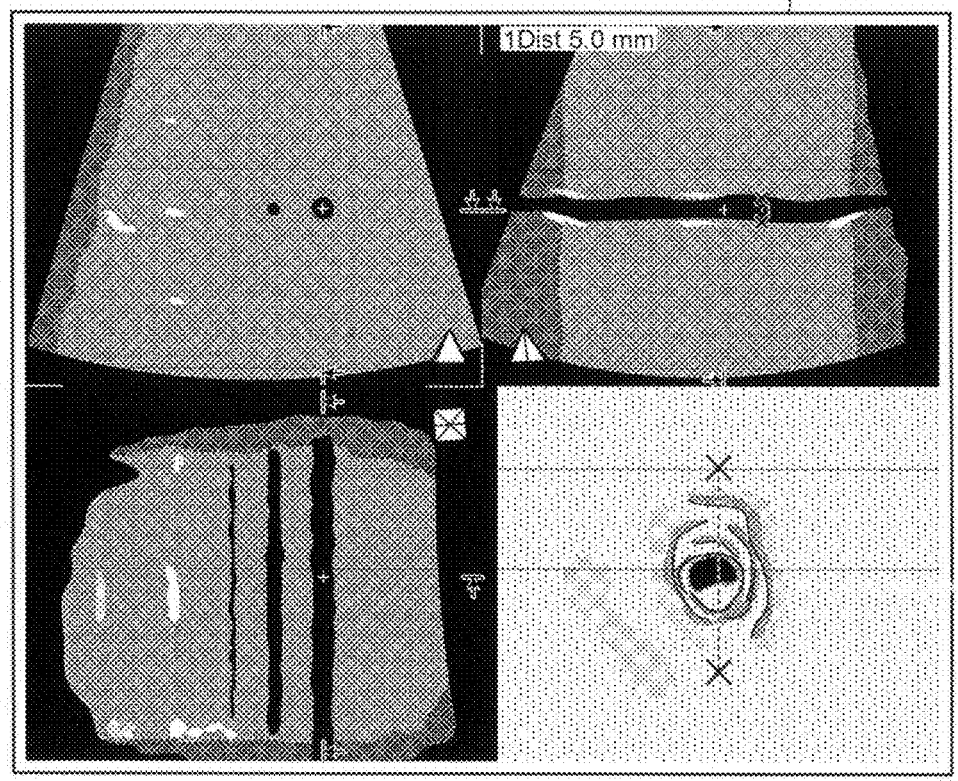
FIG. 6 is a drawing of an example of a Fly Thru display according to the first embodiment.

FIG. 6 is a drawing of an example of the Fly Thru display according to the first embodiment. In FIG. 6, the image at lower right is a Fly Thru image, whereas the images at upper right, upper left, and lower left are MPR images on three orthogonal cross-sectional planes. For example, as shown in FIG. 6, the controlling unit 17 causes the monitor 2 to display the MPR images on the three orthogonal cross-sectional planes as well as the Fly Thru image. In this situation, the ultrasound diagnosis apparatus 100 according to the first embodiment realizes a Fly Thru display in which the diameter of the lumen in the Fly Thru image is arranged to be equal to the diameter of the lumen in the MPR images in which the two points were set, as a result of the processes performed by the parameter setting unit 141.

Further, the controlling unit 17 is able to display, as a guide line, the position of the lumen internal wall set in the MPR images. For example, as shown in the lower right section in FIG. 6, the controlling unit 17 causes points to be displayed (with X's) in the positions corresponding to the two points set in the MPR images and causes a straight line connecting the two points together to be displayed.

As explained above, the ultrasound diagnosis apparatus 100 according to the first embodiment is able to realize the Fly Thru display in which the diameter of the lumen in the MPR images is arranged to be equal to the diameter of the lumen in the Fly Thru image. In this situation, the processes described above may be performed at any time during the Fly Thru display procedure. In other words, the processes may be performed immediately after the volume data is acquired, or the processes may be performed again after a Fly Thru image is once displayed.

Further, the processes may be performed all at once on the entirety of the volume data. Alternatively, the processes may be performed every time a Fly Thru image is displayed by updating the PVR images.

Next, a process performed by the ultrasound diagnosis apparatus 100 according to the first embodiment will be explained, with reference to FIG. 7. FIG. 7 is a flowchart of a procedure in the process performed by the ultrasound diagnosis apparatus 100 according to the first embodiment. As shown in FIG. 7, if the ultrasound diagnosis apparatus 100 according to the first embodiment is in a Fly Thru display mode (step S101: Yes), the controlling unit 17 judges whether two points have been set on opposing sides of the lumen internal wall of a lumen rendered in an MPR image (step S102).

If two points have been set (step S102: Yes), the controlling unit 17 measures the distance between the two points (step S103) and notifies the parameter setting unit 141 of position information of the two set points and the measured result of the distance between the two points.

Subsequently, the parameter setting unit 141 calculates a straight line in the volume data that passes through the two set points, on the basis of the notified position information of the two points (step S104). After that, the parameter setting unit 141 extracts such a threshold value that arranges the distance between the two points on the calculated straight line to be equal to the distance (the notified distance) between the two points in the MPR image (step S105).

After that, the Fly Thru image generating unit 142 generates a Fly Thru image, by using volume data generated by using the extracted threshold value (step S106). Subsequently, the controlling unit 17 causes the monitor 2 to display the generated Fly Thru image (step S107) and ends the process. While the Fly Thru display mode is off and until two points are set on opposing sides of the lumen internal wall, the ultrasound diagnosis apparatus 100 is in a standby state (step S101: No; and step S102: No).

As explained above, according to the first embodiment, the parameter setting unit 141 sets the value of the image quality adjusting parameter (the threshold value) used for generating the PVR images obtained by projecting the inside of the lumen from the predetermined viewpoints, on the basis of the information about the lumen rendered in the MPR images generated by using the volume data. Further, the Fly Thru image generating unit 142 generates the PVR images by using the value of the image quality adjusting parameter that was set. Further, the controlling unit 17 causes the monitor 2 to display the PVR images. Accordingly, the ultrasound diagnosis apparatus 100 according to the first embodiment is able to generate and display the Fly Thru image corresponding to the MPR images and makes it possible to properly display the lumen in the Fly Thru image.

In addition, according to the first embodiment, the parameter setting unit 141 sets the image quality adjusting parameter in such a manner that the distance between the two points each of which is set on a different one of the opposing sides of the internal wall of the lumen rendered in the MPR image corresponds to the distance between the two points in the volume data. Consequently, the ultrasound diagnosis apparatus 100 according to the first embodiment is able to arrange the diameter of the lumen in the MPR image to be equal to the diameter of the lumen in the Fly Thru image and thus makes it possible to more properly display the lumen in the Fly Thru image.

Furthermore, according to the first embodiment, the controlling unit 17 causes the guide line to be displayed in the Fly Thru image in the positions corresponding to the two points each of which is set on a different one of the opposing sides of the internal wall of the lumen rendered in the MPR image. Consequently, the ultrasound diagnosis apparatus 100 according to the first embodiment makes it possible to display the correspondence relationship between the MPR image and the Fly Thru image more clearly.

In the first embodiment described above, each of the points is set on a different one of the opposing sides of the internal wall of the lumen rendered in the MPR image, so as to measure the diameter of the lumen by measuring the distance between the two set points and so as to arrange the diameter of the lumen in the MPR image to be equal to the diameter of the lumen in the Fly Thru image. In a second embodiment, an example will be explained in which the lumen internal wall in volume data is arranged to match a point in an MPR image. An ultrasound diagnosis apparatus according to the second embodiment is different from the ultrasound diagnosis apparatus 100 according to the first embodiment, only in the contents of the process performed by the parameter setting unit 141 shown in FIG. 4.

The parameter setting unit 141 according to the second embodiment sets an image quality adjusting parameter in such a manner that the position of the internal wall of a lumen in volume data correspond to a point set on the internal wall of the lumen rendered in a two-dimensional image. More specifically, the parameter setting unit 141 obtains position information (coordinates) of the point in the MPR image that is set by the viewer. After that, the parameter setting unit 141 extracts the value of an image quality adjusting parameter obtained when the internal wall of the lumen is superimposed on the coordinates contained in the volume data and sets the extracted value of the image quality adjusting parameter as an image quality adjusting parameter used for generating a Fly Thru image.

Figure 8A:
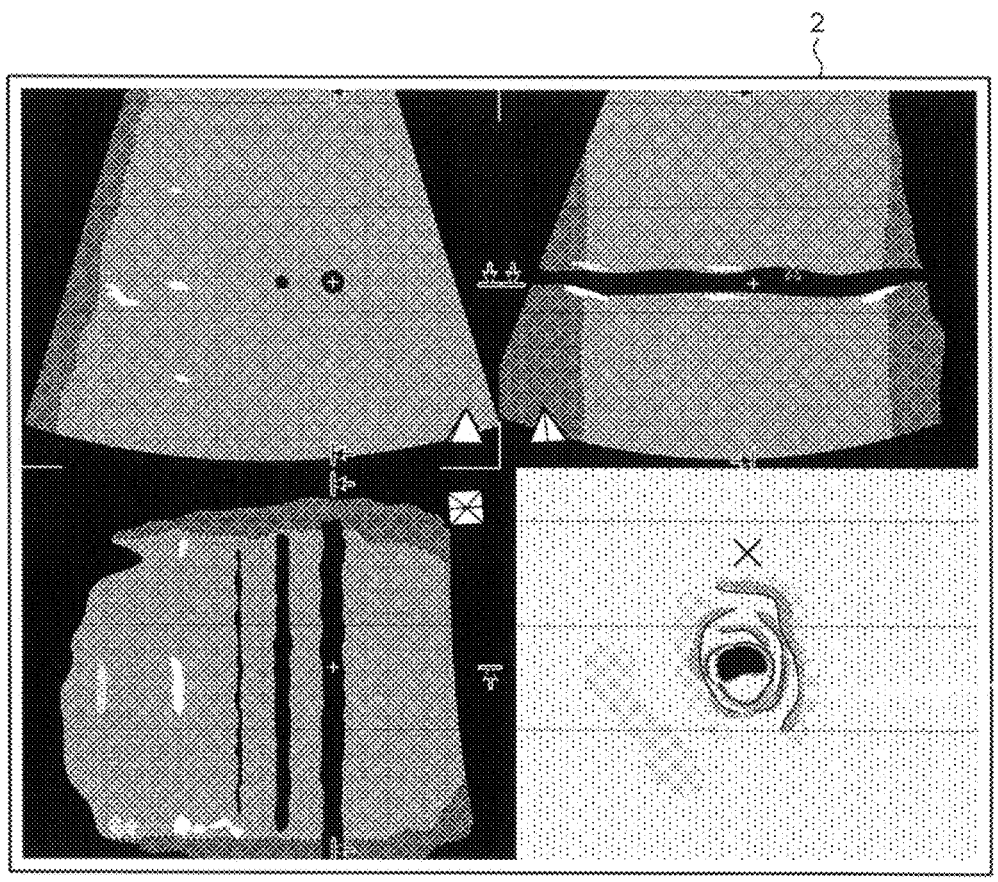
FIG. 8A is a drawing of an exemplary setting process performed on a lumen internal wall according to a second embodiment.

FIG. 8A is a drawing of an exemplary setting process performed on a lumen internal wall according to the second embodiment. For example, the viewer selects one of MPR images on three orthogonal cross-sectional planes. After that, as shown in FIG. 8A, the viewer sets a point (the X in the drawing) on the internal wall of the lumen rendered in the selected MPR image. The controlling unit 17 notifies the parameter setting unit 141 of the position information of the point set by the viewer.

Figure 8B:
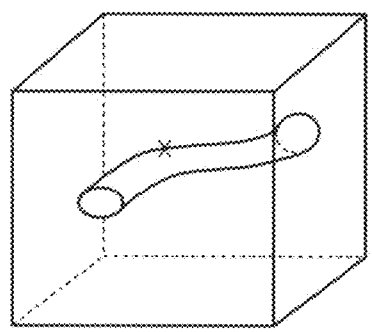
FIG. 8B is a drawing for explaining an example of a process performed by a parameter setting unit according to the second embodiment.

The parameter setting unit 141 extracts such an image quality adjusting parameter by which the internal wall of the lumen is superimposed on the notified coordinates of the point, by varying the image quality adjusting parameter for the volume data to different values. In this situation, the lumen region in the volume data is extracted in advance. FIG. 8B is a drawing for explaining an example of the process performed by the parameter setting unit 141 according to the second embodiment. For example, as shown in FIG. 8B, the parameter setting unit 141 extracts such a threshold value by which the internal wall of the lumen is superimposed on the coordinates of the point, by varying the threshold value to different values. Further, the parameter setting unit 141 sets the extracted threshold value as the threshold value used for generating the Fly Thru image.

In this situation, the set point does not necessarily have to be one. It is acceptable to set two or more points. In that situation, the parameter setting unit 141 extracts a threshold value by using each of the two or more points and sets the average of the extracted threshold values as the threshold value used for generating a Fly Thru image.

Alternatively, the parameter setting unit 141 may cause the lumen internal wall to approximate to each of the two or more set points so as to calculate such a threshold value that minimizes the distance between each of the points and the lumen internal wall by using a least squares method or the like. After that, the parameter setting unit 141 sets the calculated threshold value as the threshold value used for generating a Fly Thru image.

Next, a process performed by the ultrasound diagnosis apparatus 100 according to the second embodiment will be explained, with reference to FIG. 9. FIG. 9 is a flowchart of a procedure in the process performed by the ultrasound diagnosis apparatus 100 according to the second embodiment. As shown in FIG. 9, if the ultrasound diagnosis apparatus 100 according to the second embodiment is in a Fly Thru display mode (step S201: Yes), the controlling unit 17 judges whether a point has been set on the lumen internal wall rendered in an MPR image (step S202).

If a point has been set (step S202: Yes), the controlling unit 17 notifies the parameter setting unit 141 of position information of the set point. On the basis of the notified position information of the point, the parameter setting unit 141 generates volume data so that the lumen internal wall is superimposed on the set point (step S203). In other words, the parameter setting unit 141 extracts such a threshold value by which the internal wall of the lumen is superimposed on the coordinates of the point, by varying the threshold value to different values.

After that, the Fly Thru image generating unit 142 generates a Fly Thru image by using the volume data generated by using the extracted threshold value (step S204). Subsequently, the controlling unit 17 causes the monitor 2 to display the generated Fly Thru image (step S205) and ends the process. While the Fly Thru display mode is off and until a point is set on the lumen internal wall, the ultrasound diagnosis apparatus 100 is in a standby state (step S201: No; and step S202: No).

As explained above, according to the second embodiment, the parameter setting unit 141 sets the image quality adjusting parameter in such a manner that the position of the internal wall of the lumen in the volume data corresponds to the point set on the internal wall of the lumen rendered in the MPR image. Consequently, the ultrasound diagnosis apparatus 100 according to the second embodiment is able to realize a Fly Thru display in which the position of the lumen internal wall in the MPR image is associated with the position of the internal wall of the lumen in the Fly Thru image and thus makes it possible to properly display the lumen in the Fly Thru image.

In the first and the second embodiments described above, the examples are explained in which the one or more points are set in the MPR image. As a third embodiment, an example will be explained in which a line extending along the lumen internal wall rendered in an MPR image is set. An ultrasound diagnosis apparatus according to the third embodiment is different from the ultrasound diagnosis apparatus 100 according to the first embodiment only in the contents of the process performed by the parameter setting unit 141 shown in FIG. 4.

The parameter setting unit 141 according to the third embodiment extracts a contour line indicating the internal wall of a lumen rendered in an MPR image and sets an image quality adjusting parameter in such a manner that the position of the internal wall of the lumen in the volume data corresponds to the extracted contour line. More specifically, the parameter setting unit 141 extracts the contour line of the internal wall of the lumen rendered in the MPR image by using an edge detecting method or the like. Further, the parameter setting unit 141 obtains position information of the extracted contour line (the coordinates of all the points constituting the contour line). After that, the parameter setting unit 141 extracts the value of an image quality adjusting parameter obtained when the internal wall of the lumen is superimposed on the coordinates of all the points contained in the volume data and sets the extracted value of the image quality adjusting parameter as the image quality adjusting parameter used for generating a Fly Thru image.

Figure 10:
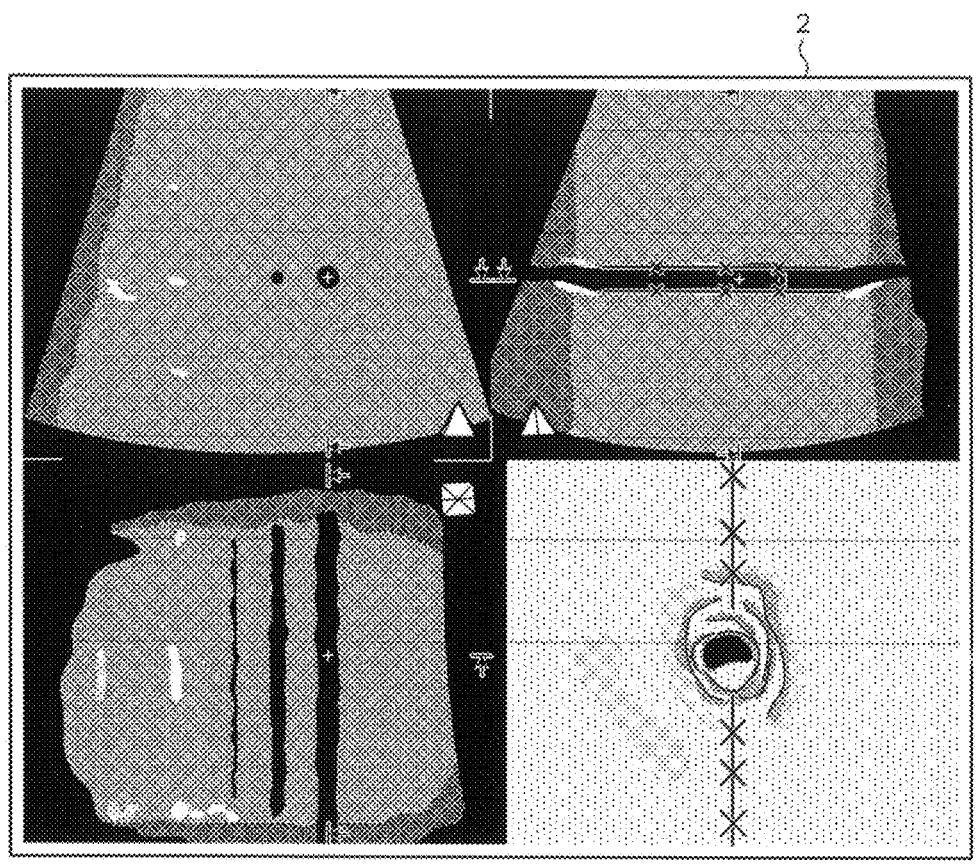
FIG. 10 is a drawing of an exemplary setting process performed on a lumen internal wall according to a third embodiment.

FIG. 10 is a drawing of an exemplary setting process performed on a lumen internal wall according to the third embodiment. For example, the parameter setting unit 141 selects an image in which a contour line is to be extracted, from among MPR images on three orthogonal cross-sectional planes. After that, as shown in FIG. 10, the parameter setting unit 141 extracts the contour line of the internal wall of the lumen rendered in the selected MPR image, by using an edge detecting method or the like.

The parameter setting unit 141 extracts a threshold value by using each of the points constituting the extracted contour line and sets the average of the extracted threshold values as the threshold value used for generating the Fly Thru image. Alternatively, the parameter setting unit 141 may cause the lumen internal wall to approximate to each of the plurality of points so as to calculate such a threshold value that minimizes the distance between each of the points and the lumen internal wall by using a least squares method or the like. After that, the parameter setting unit 141 sets the calculated threshold value as the threshold value used for generating a Fly Thru image.

As explained above, the ultrasound diagnosis apparatus 100 according to the third embodiment sets the image quality adjusting parameter in such a manner that the position of the lumen internal wall corresponds to the contour line indicating the lumen internal wall. For example, an arrangement is acceptable in which the image quality adjusting parameter setting process according to the third embodiment is automatically performed, so that the viewer fine-tunes the image quality adjusting parameter through the image quality adjusting parameter setting process according to the first or the second embodiment.

As explained above, according to the third embodiment, the parameter setting unit 141 extracts the contour line indicating the internal wall of the lumen rendered in the MPR image and sets the image quality adjusting parameter in such a manner that the position of the internal wall of the lumen in the volume data corresponds to the extracted contour line. Consequently, the ultrasound diagnosis apparatus 100 according to the third embodiment makes it possible to cause the lumen internal wall in the MPR image to be automatically associated with the lumen internal wall in the Fly Thru image.

The first, the second, and the third embodiments have thus been explained. However, the disclosure herein may be embodied in other various modes other than those in the first, the second, and the third embodiments.

In the first embodiment described above, the example in which the guide line is displayed in the Fly Thru image is explained. However, possible embodiments are not limited to this example. For instance, it is also acceptable to cause the range of a field of view of a Fly Thru image currently being displayed or an alert to be displayed in an MPR image.

Figure 11:
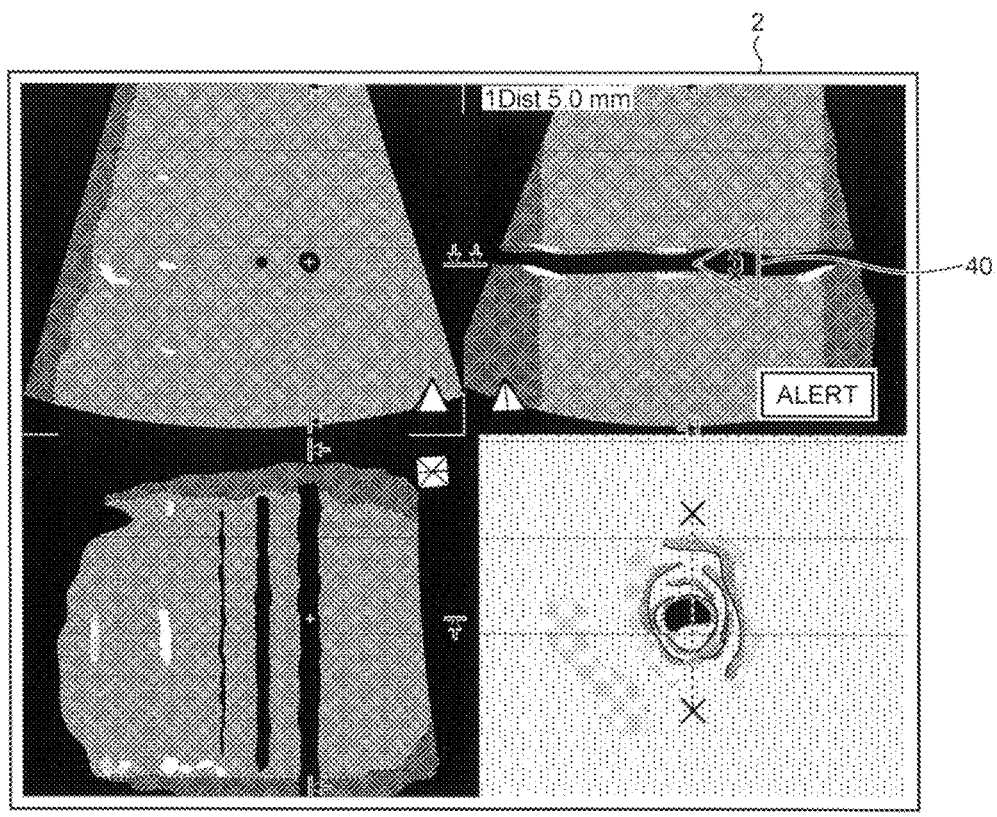
FIG. 11 is a drawing of an exemplary display according to a fourth embodiment.

FIG. 11 is a drawing of an exemplary display according to a fourth embodiment. For example, as shown in FIG. 11, the controlling unit 17 causes the range of a field of view 40 of a Fly Thru image currently being displayed to be displayed while being superimposed on an MPR image. As a result, when the viewer needs to re-set a point, it is possible to present to the viewer an appropriate location in which the point should be set.

In addition, as shown in FIG. 11, the controlling unit 17 causes an alert to be displayed while being superimposed on the MPR image. In an example, during a point setting process, if the viewer sets a point in a position that does not correspond to the lumen internal wall (e.g., in a tissue), the controlling unit 17 causes an alert to be displayed, as shown in FIG. 11. In that situation, the internal storage unit 16 has stored therein, in advance, the threshold value for the brightness levels used for determining the location outside the lumen.

After that, when the viewer has set a point, the controlling unit 17 judges whether the brightness level of the point corresponds to the outside of the lumen or not, by referring to the threshold value. In this situation, if the set point is determined to correspond to the outside of the lumen, the controlling unit 17 causes the monitor 2 to display an alert.

Alternatively, the internal storage unit 16 may store therein, in advance, a threshold value for the brightness levels used for determining if a point corresponds to the lumen. In that situation, when the viewer has set a point, the controlling unit 17 judges whether a region (i.e., the lumen) having brightness levels lower than the threshold value is present near the set point, by referring to the threshold value. If no region having brightness levels lower than the threshold value is present (i.e., if the lumen is not present) near the set point, the controlling unit 17 causes the monitor 2 to display an alert.

As explained above, when the point set by the viewer is erroneously set, the alert is displayed. Consequently, it is possible to display, without failure, an image in which the lumen internal wall in the MPR image is arranged to match the lumen internal wall in the Fly Thru image.

In the first to the third embodiments described above, the examples in which the threshold value is used as the image quality adjusting parameter are explained. However, possible embodiments are not limited to those examples. For example, it is acceptable to use transmittance or a gamma value as an image quality adjusting parameter. The transmittance is a parameter used for adjusting the slope of the chart in FIG. 2 indicating the relationship between the threshold values and the brightness levels. The gamma value is a parameter used for adjusting the state (e.g., linear, curved, etc.) of the slope portion of the chart shown in FIG. 2.

In the first to the third embodiments described above, the examples are explained in which the parameter setting unit 141 sets the value of the image quality adjusting parameter (e.g., the threshold value), generates the Fly Thru image by using the value of the image quality adjusting parameter that was set, and displays the generated Fly Thru image. It is also acceptable to further configure the ultrasound diagnosis apparatus 100 according to the fourth embodiment so that the image quality adjusting parameter can manually be fine-tuned.

More specifically, the input device 3 receives an adjustment instruction indicating that an adjustment should further be made to the value of the image quality adjusting parameter set by the parameter setting unit 141. In this situation, for example, the input device 3 is configured with a rotary encoder, a trackball, a dial, a GUI, and the like and is configured to receive the adjustment instruction indicating that the value of the image quality adjusting parameter such as a threshold value should be increased or decreased.

In an example, the parameter setting unit 141 first sets the value of an image quality adjusting parameter (e.g., a threshold value) by using the information about the positions of the two points in the MPR image and the measured result notified by the controlling unit 17. Further, the Fly Thru image generating unit 142 generates PVR images by using the value of the image quality adjusting parameter that was set. The controlling unit 17 causes the monitor 2 to display a Fly Thru image in which the generated PVR images are displayed as a moving image.

In this situation, the viewer is able to fine-tune the image quality adjusting parameter via the input device 3, while viewing the displayed Fly Thru image. In other words, the input device 3 receives the adjustment instruction indicating that the value of the image quality adjusting parameter should be increased or decreased according to an operation by the viewer. In this situation, the adjustment made through the input device 3 to increase or decrease the value of the image quality adjusting parameter may be an image quality adjusting parameter itself such as a threshold value or may be a distance between two sides of the wall of the lumen.

When the input device 3 has received the adjustment instruction to increase or decrease the value of the image quality adjusting parameter, the Fly Thru image generating unit 142 changes the current value of the image quality adjusting parameter by an amount indicated in the received adjustment instruction and generates PVR images obtained by projecting the inside of the lumen while using the value after the change. The controlling unit 17 then causes the monitor 2 to display a Fly Thru image with the newly-generated PVR images.

In this situation, when the Fly Thru image generating unit 142 has generated the PVR images reflecting the adjustment instruction, the diameter of the lumen estimated from the new adjustment instruction will be different. Thus, when having received the adjustment instruction, the controlling unit 17 makes an adjustment also to the markers displayed in the MPR images and to the positions of the points arranged in the MPR images, before having the MPR images displayed on the monitor 2. In other words, the controlling unit 17 makes the adjustment (increases/decreases the diameter) corresponding to the adjustment instruction to the diameter of the lumen rendered in each of the MPR images on the three orthogonal cross-sectional planes, before having the MPR images displayed on the monitor 2. In one example, when the threshold value has been adjusted, the controlling unit 17 moves the positions of the markers arranged in the MPR images and the markers for measuring between the two points, in accordance with the adjustment made to the threshold value.

In this situation, the input device 3 is also able to receive an operation to set two points in the newly-displayed MPR images. Further, the controlling unit 17 is able to cause the initially-set two points to be continuously displayed in the adjusted MPR images. The controlling unit 17 is also able to have the points displayed in a different color, in a blinking mode, or in a different size.

As a result, the viewer is able to view the Fly Thru image and the MPR images in which the lumen is displayed more properly. In the example described above, the two points are set in the MPR images; however, the embodiment is also applicable to a situation where one point is set in an MPR image or where the contour line of the internal wall of the lumen is extracted from an MPR image.

Further, in the situation where the contour line of the internal wall of the lumen is extracted, the input device 3 is also able to receive an adjustment instruction regarding fine-tuning the contour line of the internal wall in the MPR image.

As explained above, the ultrasound diagnosis apparatus 100 disclosed herein makes it possible to properly display the lumen in the Fly Thru image; however, possible embodiments are not limited to those examples. For example, the disclosure herein can be generalized and applied to other sites besides lumens.

More specifically, the ultrasound diagnosis apparatus 100 disclosed herein may be configured so that the parameter setting unit 141 sets the value of an image quality adjusting parameter used for generating a projection image obtained by projecting a site from a predetermined viewpoint, on the basis of information about the site rendered in a two-dimensional tomographic image generated by using three-dimensional image data. Further, the image generating unit 14 generates the projection image by using the value of the image quality adjusting parameter that was set. After that, the controlling unit 17 causes the monitor 2 to display the projection image.

For example, the parameter setting unit 141 sets the value of an image quality adjusting parameter used for generating a Volume Rendering (VR) image by using one or more points or a contour line set in an MPR image of the face of a baby in a fetal echo test. The image generating unit 14 generates the VR image by using the value of the image quality adjusting parameter that was set. The controlling unit 17 causes the monitor 2 to display the generated VR image. In this situation, the input device 3 is able to receive an adjustment instruction to fine-tune the image quality adjusting parameter, in the same manner as in the examples described above.

The embodiments described above are merely examples and possible embodiments are not limited to those examples. In other words, the ultrasound diagnosis apparatus 100 is able to apply the methods described above to various situations. For example, the parameter setting unit 141 may set the value of an image quality adjusting parameter used for generating a VR image of the surface of the liver, by using one or more points or a contour line set in an MPR image of the liver. The image generating unit 14 then generates the VR image by using the value of the image quality adjusting parameter that was set. Subsequently, the controlling unit 17 causes the monitor 2 to display the generated VR image.

In the first to the third embodiments described above, the examples are explained in which the ultrasound diagnosis apparatus sets the image quality adjusting parameter; however, the processes described above may be performed by an image processing apparatus such as a workstation. In that situation, for example, the workstation that is connected, via a network, to the ultrasound diagnosis apparatus or to the image storing apparatus obtains the volume data from the ultrasound diagnosis apparatus or from the image storing apparatus. The workstation then performs the processes described above by using the obtained volume data.

As explained above, according to an aspect of the first, the second, the third, and the fourth embodiments, the ultrasound diagnosis apparatus, the image processing apparatus, and the computer program disclosed herein make it possible to properly display the lumen in the Fly Thru image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus, comprising:
    processing circuitry configured to
        generate three-dimensional image data based on reflected-wave data received by an ultrasound probe,
        generate a two-dimensional tomographic image using the three-dimensional image data,
        set a value of an image quality adjusting parameter used for generating a virtual endoscopic image so that a position of an internal wall of a lumen in the three-dimensional image data matches a corresponding position of the internal wall of the lumen in the two-dimensional tomographic image or so that a distance between two points on opposing sides of the internal wall of the lumen in the three-dimensional image data is equal to a corresponding distance between two points set in the two-dimensional tomographic image;
        generate the virtual endoscopic image by projecting an inside of the lumen from a predetermined viewpoint and using the value of the set image quality adjusting parameter; and
        cause a predetermined display to display the virtual endoscopic image.

2. The ultrasound diagnosis apparatus according to claim 1, wherein the processing circuitry is further configured to set the value of the image quality adjusting parameter so that the distance between the two points, each of which is on a different one of opposing sides of the internal wall of the lumen in the three-dimensional image data is equal to the corresponding distance between the two points, each of which is set on the different one of the opposing sides of the internal wall of the lumen in the two-dimensional tomographic image.

3. The ultrasound diagnosis apparatus according to claim 2, wherein the processing circuitry is further configured to cause the predetermined display to display an alert suggesting an erroneous setting, when a brightness level at a point set in the two-dimensional tomographic image exceeds a predetermined threshold value.

4. The ultrasound diagnosis apparatus according to claim 2, wherein the processing circuitry is further configured to cause a guide line to be displayed on a line connecting two points in the virtual endoscopic image that correspond to the two points, each of which is set on a different one of the opposing sides of the internal wall of the lumen rendered in the two-dimensional tomographic image.

5. The ultrasound diagnosis apparatus according to claim 1, wherein the processing circuitry is further configured to set the value of the image quality adjusting parameter so that a portion of the internal wall of the lumen in the three-dimensional image data is located at a position in the three-dimensional image data having coordinates corresponding to a point set on the internal wall of the lumen in the two-dimensional tomographic image.

6. The ultrasound diagnosis apparatus according to claim 1, wherein the processing circuitry is further configured to extract a contour line indicating the internal wall of the lumen in the two-dimensional tomographic image and set the value of the image quality adjusting parameter so that a portion of the internal wall of the lumen in the three-dimensional image data is located at positions in the three-dimensional image data corresponding to positions of the extracted contour line in the two-dimensional tomographic image.

7. The ultrasound diagnosis apparatus according to claim 1, wherein
    the processing circuitry is further configured to generate the virtual endoscopic image by using an adjusted value of the set value of the image quality adjusting parameter, the set value being adjusted to obtain the adjusted value based on an adjustment instruction.

8. The ultrasound diagnosis apparatus according to claim 7, wherein the processing circuitry is further configured to cause, in accordance with generation of the virtual endoscopic image reflecting the adjustment instruction, the predetermined display to display a two-dimensional tomographic image generated based on the adjusted value.

9. An image processing apparatus, comprising:
    processing circuitry configured to
        acquire three-dimensional image data generated based on reflected-wave data received by an ultrasound probe,
        generate a two-dimensional tomographic image using the three-dimensional image data,
        set a value of an image quality adjusting parameter used for generating a virtual endoscopic image so that a position of an internal wall of a lumen in the three-dimensional image data matches a corresponding position of the internal wall of the lumen in the two-dimensional tomographic image or so that a distance between two points on opposing sides of the internal wall of the lumen in the three-dimensional image data is equal to a corresponding distance between two points set in the two-dimensional tomographic image;

generate the virtual endoscopic image by projecting an inside of the lumen from a predetermined viewpoint and using the value of the set image quality adjusting parameter; and cause a predetermined display to display the virtual endoscopic image.

10. An ultrasound diagnosis apparatus, comprising:
processing circuitry configured to
generate three-dimensional image data based on reflected-wave data received by an ultrasound probe,
generate a two-dimensional tomographic image using the three-dimensional image data,
set a value of an image quality adjusting parameter used for generating a projection image so that a position of a site in the three-dimensional image data matches a corresponding position of the site in the two-dimensional tomographic image;
generate the projection image by projecting the site from a predetermined viewpoint and using the value of the set image quality adjusting parameter; and
cause a predetermined display to display the projection image.

* * * * *